(12) United States Patent
Sternberger

(10) Patent No.: US 11,324,430 B2
(45) Date of Patent: May 10, 2022

(54) SENSOR-BASED ISCHEMIA DETECTION

(71) Applicant: The Johns Hopkins University, Baltimore, MD (US)

(72) Inventor: Wayne I. Sternberger, Highland, MD (US)

(73) Assignee: The Johns Hopkins University, Baltimore, MD (US)

( * ) Notice: Subject to any disclaimer, the term of this patent is extended or adjusted under 35 U.S.C. 154(b) by 267 days.

(21) Appl. No.: 16/190,733

(22) Filed: Nov. 14, 2018

(65) Prior Publication Data

US 2019/0216354 A1  Jul. 18, 2019

Related U.S. Application Data

(60) Provisional application No. 62/617,344, filed on Jan. 15, 2018.

(51) Int. Cl.
*A61B 5/296* (2021.01)
*A61B 5/316* (2021.01)
(Continued)

(52) U.S. Cl.
CPC .............. *A61B 5/296* (2021.01); *A61B 5/316* (2021.01); *A61B 5/389* (2021.01); *A61B 5/004* (2013.01);
(Continued)

(58) Field of Classification Search
CPC ......... A61B 5/0488; A61B 5/477; A61B 5/68; A61B 5/87; A61B 5/4511; A61B 5/004;
(Continued)

(56) References Cited

U.S. PATENT DOCUMENTS 9,778,131 B2   10/2017   Everett et al.
9,881,133 B2   1/2018    Graventein et al.
(Continued)

FOREIGN PATENT DOCUMENTS

WO   WO2017151856      9/2017
WO   WO2018046324      3/2018
WO   WO-2018046324 A1 * 3/2018  .............. A61B 5/445

OTHER PUBLICATIONS

Rouffet, EMG normalization to study muscle activation in cycling, Mar. 20, 2007, Journal of Electromyography and Kinesiology, 18, 866-878 (Year: 2008).*

(Continued)

*Primary Examiner* — Christian Jang
*Assistant Examiner* — Anna Roberts
(74) *Attorney, Agent, or Firm* — Todd R. Farnsworth

(57) ABSTRACT

Example apparatuses, systems, and methods for detecting a muscle tissue ischemia event are provided. An example apparatus may include an electromyography (EMG) sensor applied to a patient to detect electrical activity in the muscle tissue. The apparatus may also include processing circuitry in communication with the EMG sensor and configured to receive EMG signals from the EMG sensor and detect characteristics within the EMG signals indicating oxygen depletion within the muscle tissue of the patient. The characteristics may include a signal power level of the EMG signals increasing by at least a threshold value at a select frequency or with respect to a select band of frequencies. The processing circuitry may be further configured to trigger an output, in response to detecting the characteristics, indicating that the oxygen depletion in the muscle tissue is indicative of an ischemia event.

20 Claims, 8 Drawing Sheets

(51) Int. Cl.
    *A61B 5/389*     (2021.01)
    *A61B 5/00*     (2006.01)
    *A61B 5/1455*     (2006.01)

(52) U.S. Cl.
    CPC ........... *A61B 5/14551* (2013.01); *A61B 5/447* (2013.01); *A61B 2562/0271* (2013.01)

(58) Field of Classification Search
    CPC .. A61B 2562/0271; A61G 7/05; A61G 7/057; A61G 7/05761; A61G 7/05769; A61G 7/0573; A47C 27/083
    USPC ........................................................ 600/546
    See application file for complete search history.

(56) References Cited

U.S. PATENT DOCUMENTS

| | | | |
|---|---|---|---|
| 9,888,869 | B2 | 2/2018 | Sternberger |
| 10,004,447 | B2 | 7/2018 | Larson et al. |
| 2007/0027371 | A1* | 2/2007 | Benaron ............... A61B 5/0031 600/310 |
| 2007/0260289 | A1* | 11/2007 | Giftakis ................ A61B 5/369 607/45 |
| 2008/0300571 | A1 | 12/2008 | LePivert |
| 2010/0162832 | A1 | 7/2010 | Brauers |
| 2012/0190989 | A1 | 7/2012 | Kaiser et al. |
| 2013/0066168 | A1 | 3/2013 | Yang et al. |
| 2016/0228050 | A1 | 8/2016 | Binay et al. |
| 2016/0259905 | A1* | 9/2016 | Park ......................... A61B 5/01 |
| 2017/0157431 | A1* | 6/2017 | Cheatham, III ....... A61N 2/002 |
| 2017/0224271 | A1 | 8/2017 | Lachenbruch et al. |
| 2020/0391021 | A1* | 12/2020 | Sachs ................... A61N 1/3606 |

OTHER PUBLICATIONS

T. Beck et al., "Shifts in EMG Spectral Power During Fatiguing Dynamic Contractions", Muscle Nerve 50: 95-102, published online on Oct. 12, 2013, Wiley Periodicals.

G. Dimitrov et al., "Muscle Fatigue During Dynamic Contractions Assessed by New Spectral Indices", Applied Sciences Biodynamics, Medicine & Science in Sports & Exercise, May 2006, pp. 1971-1979.

M. Kramer et al., Intramuscular Pressure, Tissue Oxgenation and EMG Fatigue Measured During Isometric Fatigue-Inducing Contraction of the Multifidus Muscle, Eur Spine J (2005) 14: 578-585, Springer-Verlag 2005.

J. Meyer et al., "Textile Pressure Sensor for Muscle Activity and Motion Detection", 2006 IEEE, 5 pages.

T. Sadamoto et al., "Skeletal Muscle Tension, Flow, Pressure, and EMG During Sustained Isometric Contractions in Humans", European Journal of Applied Physiology (1983) 51: 395-408.

M. Gonzalez-Izal et al., "EMG Spectral Indices and Muscle Power Fatigue During Dynamic Contractions", Elsevier, Journal of Electromyography and Kinesiology 20 (2010) 233-240.

Haridy, "Humon Hex fitness tracker measures muscle oxygen levels," New Atlas, Jan. 7, 2018, available at https://newatlas.com/humon-hex-muscle-oxygen-wearable/52850/, last accessed Apr. 16, 2019.

* cited by examiner

SENSOR-BASED ISCHEMIA DETECTION

CROSS-REFERENCE TO RELATED APPLICATIONS

This application claims the benefit of U.S. Provisional Application No. 62/617,344 filed on Jan. 15, 2018, the entire contents of which are hereby incorporated herein by reference.

STATEMENT OF GOVERNMENTAL INTEREST

This invention was made with U.S. Government support under grant number 1P30HS023553-01 awarded by the U.S. Department of Health and Human Services. The government has certain rights in the invention.

TECHNICAL FIELD

Example embodiments generally relate to biologic analysis using sensors and, in particular, relate to using sensors to detect changes in soft tissue of a patient indicative of the formation of an ischemia.

BACKGROUND

Pressure ulcers, also known as bed sores, can form when soft tissues (e.g., skin or muscle) die due to a lack of blood supply, and more specifically, a lack of oxygen perfusion to the affected soft tissue. Inadequate blood supply to soft tissue may be referred to as an ischemia. In the context of pressure ulcers, an ischemia may be induced by layers of soft tissue being compressed between a focused external pressure (e.g., from a bed and the weight of a patient) and a hard tissue (e.g., a bone) in manner that prevents blood flow to the area. Vascularization in the body often profuses through muscle and ultimately feeds to the skin. During an ischemia event, muscle can survive for only a short time (e.g., on the order of 1 to 2 hours) relative to the skin (e.g., on the order of 12 hours).

Conventional techniques for proactively preventing such pressure ulcers can involve physically moving or repositioning a patient according to a schedule to assure that perfusion or reperfusion of oxygen to the soft tissue occurs prior to tissue death. After taking such measures, recovery to the soft tissue that was affected by an ischemia may be begin, which fortunately occurs more quickly than degradation of the soft tissue. Accordingly, the movement or repositioning schedule for patients may be selected such that the frequency of movement and repositioning is likely to prevent the creation of pressure ulcers.

Typically, a pressure ulcer is diagnosed through visual inspection of the skin and other externally observable indicators associated with tissue injury. Unfortunately, external tissue (e.g., skin) reveals visual indications after internal soft tissue (e.g., muscle) has been affected or even already died. Therefore, diagnosing muscle death due to pressure ulcers is often performed indirectly through external indication on the skin, which is often too late. Accordingly, there is a need for a technical advance that will facilitate the detection of ischemia in soft tissue, both externally and internally, before external, observable indications are presented and the internal soft tissue has already died.

BRIEF SUMMARY OF SOME EXAMPLES

According to some example embodiments, an apparatus for detecting an ischemia event in muscle tissue of a patient is provided. The apparatus may comprise an electromyography (EMG) sensor applied to the patient to detect electrical activity in the muscle tissue, and processing circuitry in communication with the EMG sensor. The processing circuitry may be configured to receive EMG signals from the EMG sensor and detect characteristics within the EMG signals indicating oxygen depletion within the muscle tissue of the patient. In this regard, the characteristics may include a signal power level of the EMG signals increasing by at least a threshold value (or amount) at a select frequency or with respect to a select band of frequencies. The processing circuitry may also be configured to trigger an output, in response to detecting the characteristics, indicating that the oxygen depletion is indicative of an ischemia event in the muscle tissue of the patient.

According to some example embodiments, an example method for detecting an ischemia event in muscle tissue of a patient is provided. The method may comprise receiving EMG signals at processing circuitry from an EMG sensor applied to the patient to detect electrical activity in the muscle tissue and detecting, by the processing circuitry, characteristics within the EMG signals indicating oxygen depletion within the muscle tissue of the patient. In this regard, the characteristics may include the signal power level of the EMG signals in the frequency domain increasing by at least a threshold value at a select frequency or with respect to a select band of frequencies. The example method may further include, in response to detecting the characteristics, triggering an output indicating that the oxygen depletion is indicative of an ischemia event in the muscle tissue of the patient.

According to some example embodiments, an example system for detecting an ischemia event in muscle tissue of a patient is provided. The example system may comprise a plurality of sensors outputting a plurality of respective signals and processing circuitry. The plurality of sensors may include an EMG sensor applied to the patient to detect electrical activity in the muscle tissue. The processing circuitry may be in communication with the plurality of sensors, and the processing circuitry may be configured to receive the respective signals from the plurality of sensors. The respective signals may include EMG signals from the EMG sensor. The processing circuitry may be further configured to determine an EMG factor by detecting characteristics within the EMG signals indicating oxygen depletion within the muscle tissue of the patient. The characteristics may include the signal power level of the EMG signals increasing by at least a threshold value at a select frequency or with respect to a select band of frequencies. The processing circuitry may be further configured to integrate the EMG factor with other factors to determine whether an ischemia event is occurring in the muscle tissue of the patient. The other factors may be based on the respective signals from the other sensors within the plurality of sensors. The processing circuitry may be further configured to trigger an output indicating that the ischemia event is occurring in the muscle tissue of the patient based on the integration of the EMG factor with the other factors.

BRIEF DESCRIPTION OF THE SEVERAL VIEWS OF THE DRAWING(S)

Having thus described some embodiments in general terms, reference will now be made to the accompanying drawings, which are not necessarily drawn to scale, and wherein:

DETAILED DESCRIPTION

Figure 1:
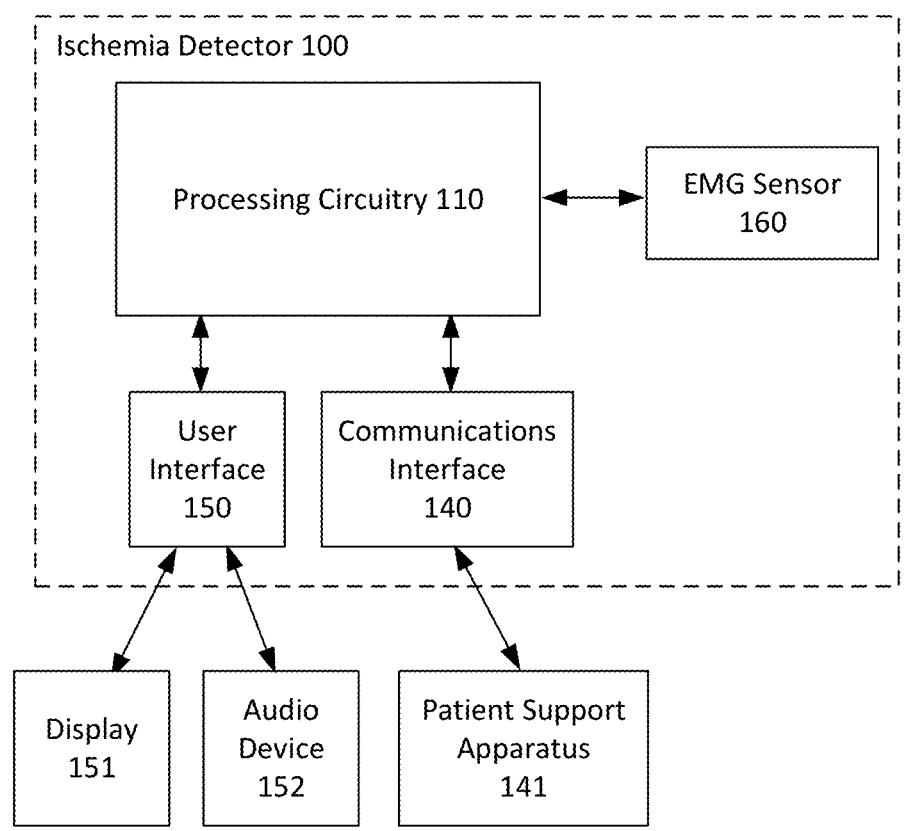
FIG. 1 illustrates a block diagram of an example apparatus in the form of an ischemia detector according to some example embodiments.

Some example embodiments now will be described more fully hereinafter with reference to the accompanying drawings, in which some, but not all example embodiments are shown. Indeed, the examples described and pictured herein should not be construed as being limiting as to the scope, applicability or configuration of the present disclosure. Rather, these example embodiments are provided so that this disclosure will satisfy applicable legal requirements. Like reference numerals refer to like elements throughout.

According to various example embodiments, apparatuses, methods, and systems are provided that facilitate an ability to detect, in real-time, oxygen depletion in muscle tissue and an ischemia event to prevent muscle tissue death, before externally observable indications are presenting. To do so, according to some example embodiments, various sensors, such as an electromyography (EMG) sensor, may be operably coupled to and controlled by a processing circuitry to detect changes in the muscle tissue that can occur during an ischemia event. The EMG sensor may be configured to detect muscle tissue function, such as muscle function under the skin, using electrodes that detect a potential or voltage difference between the electrodes which is indicative of muscle tissue movement, including involuntary movement in the muscle that occurs regularly. As such, the EMG sensor may be a surface EMG sensor that is placed on the skin of the patient at select positions near or immediately on or over the muscle tissue of interest in order to detect the muscle tissue activity. In this regard, the signal provided by the EMG sensor may be analyzed by the processing circuitry. In this regard, the signal power level may be analyzed over time and if an increase in EMG signal power level is detected, for example, at selected frequencies or frequency bands of interest, an output may be triggered that indicates that an ischemia event may be occurring. Such an analysis may be performed by leveraging analog devices to determine the power level in the time domain, or the signals may be transformed into processed EMG signals in the frequency domain to perform the analysis. An increase in the EMG signal power level may be indicative of the muscle tissue being depleted of oxygen and thus the occurrence of an ischemia event. Accordingly, a relationship between the EMG signal power level and the existence of an ischemia event can be defined. Further, due to noise and other causes of fluctuations in the EMG signal power level, according to some example embodiments, the EMG signal power level may be monitored to detect an increase by a threshold value, at a select frequency or frequency band, before the output is triggered indicating that the ischemia event has occurred. Further, according to some example embodiments, the EMG signal power level may be monitored for an increase by the threshold value for a select duration of time before the output is triggered indicating that the ischemia event has occurred, possibly while removing from consideration changes that may cause the EMG signal power level change due to noise and other events that are not relevant to the analysis.

The signals provided by other sensors may also be leveraged in a system to further assist in determining whether an ischemia event is occurring. In this regard, the processing circuitry may be configured to consider the output signals of, for example, a temperature sensor, a pressure sensor, an image sensor, an oximeter sensor, or the like, as factors in an ischemia event determination. For example, a decrease in temperature in the area of the muscle tissue may be a factor for consideration that could be indicative of an ischemia event. A detected increase in the pressure in the muscle tissue due to, for example, the weight of the patient on the area near or immediately above and adjacent the muscle tissue may be a factor for consideration in determining the occurrence of an ischemia event. Also, a change in the appearance of the skin (e.g., a change in the spectral characteristics) as determined through analysis of repeatedly captured images of the skin near or immediately above or adjacent the muscle tissue may be a factor in determining whether an ischemia event is occurring. These, and possibly other, factors may be considered, along with the determination made based on the EMG signal analysis, by the processing circuitry and integrated to formulate a multi-input determination of an ischemia event.

Accordingly, via an EMG sensor and the supporting circuitry for signal analysis, a technical solution may be provided for detecting an ischemia event in muscle tissue internal to the body. A technical solution, according to some example embodiments, may operate, according to some example embodiments, to non-invasively measure muscle perfusion through sensor output signal analysis. In this manner, ischemia events may be detected earlier and remedial measures may be triggered to limit or even prevent the occurrence of pressure ulcers in patients.

FIG. 1 illustrates a block diagram of an example apparatus in the form of an ischemia detector 100 according to some example embodiments. The ischemia detector 100 may be generally configured to control and obtain feedback from an EMG sensor 160 in an effort to detect oxygen depletion in muscle tissue and thus an ischemia event, according to some example embodiments, in real-time. The ischemia detector 100 may include a processing circuitry 110 and an EMG sensor 160. According to some example embodiments, the ischemia detector 100 may also include a user interface 150 and a communications interface 140.

The processing circuitry 110 may be in operative communication with the EMG sensor 160, and, in some example embodiments, a communications interface 140 and a user interface 150. The processing circuitry 110 may interact with or embody a memory and a processor. The processing circuitry 110 may be configurable to perform various operations as described herein. In this regard, the processing circuitry 110 may be configured to perform computational processing and memory management according to some example embodiments to facilitate performing various functionalities. In some embodiments, the processing circuitry 110 may be embodied as a chip or chip set. In other words, the processing circuitry 110 may comprise one or more physical packages (e.g., chips) including materials, components or wires on a structural assembly (e.g., a baseboard). According to some example embodiments, the processing circuitry 110 may be a computing cluster that includes a number of processors configured to operate in parallel to more rapidly complete tasks. The processing circuitry 110 may be configured to receive inputs such as from the EMG sensor 160, perform actions based on the inputs, and generate outputs to, for example, the user interface 150 or the like. In an example embodiment, the processing circuitry 110 may include one or more instances of a processor, associated circuitry, and a memory. As such, the processing circuitry 110 may be embodied as a circuit chip (e.g., an integrated circuit chip, such as a field programmable gate array (FPGA)) configured (e.g., with hardware, software or a combination of hardware and software) to perform operations described herein. Further, in some example embodiments, the processing circuitry 110 may be a configuration of components including analog components. In this regard, for example, in-band measurements, as further described below, may be made using an analog band-pass filter in operation with an integrator (e.g., a leaky integrator). Further, operational amplifiers and other passive components, such as resistors and capacitors, may also be included to support the operation and functionalities performed by the processing circuitry 110 as described herein. As such, the processing circuitry 110 may be configured to perform signal conditioning and processing using either analog or digital techniques.

In an example embodiment, the memory may include one or more non-transitory memory devices such as, for example, volatile or non-volatile memory that may be either fixed or removable. The memory may be configured to store information, data, applications, instructions or the like for enabling, for example, test scenario simulations and the like to carry out various functions in accordance with example embodiments. For example, the memory could be configured to buffer input data for processing by the processing circuitry 110. Additionally or alternatively, the memory could be configured to store instructions for execution by the processing circuitry 110. Among the contents of the memory, applications may be stored for execution by the processing circuitry 110 in order to carry out the functionality associated with each respective application.

As mentioned above, the processing circuitry 110 may be embodied in a number of different ways. For example, the processing circuitry 110 may be embodied as various processing means such as one or more processors that may be in the form of a microprocessor or other processing element, a coprocessor, a controller or various other computing or processing devices including integrated circuits such as, for example, an ASIC (application specific integrated circuit), an FPGA, or the like. In an example embodiment, the processing circuitry 110 may be configured to execute instructions stored in the memory or otherwise accessible to the processing circuitry 110. As such, whether configured by hardware or by a combination of hardware and software, the processing circuitry 110 may represent an entity (e.g., physically embodied in circuitry—in the form of processing circuitry 110) capable of performing operations according to example embodiments while configured accordingly. Thus, for example, when the processing circuitry 110 is embodied as an ASIC, FPGA, or the like, the processing circuitry 110 may be specifically configured hardware for conducting the operations described herein. Alternatively, as another example, when the processing circuitry 110 is embodied as an executor of software instructions, the instructions may specifically configure the processing circuitry 110 to perform the operations described herein.

The communications interface 140 may include one or more interface mechanisms for enabling communication with other devices external to ischemia detector 100, via, for example, a network, such as a local area network. In some cases, the communication interface 140 may be any means such as a device or circuitry embodied in either hardware, or a combination of hardware and software that is configured to receive or transmit data from/to devices in communication with the processing circuitry 110. The communications interface 140 may be a wired or wireless interface and may support various communications protocols. Communications interface 140 may be operably coupled to an antenna to support wireless communications to other components. In this regard, the communications interface 140 and the antenna may support communications via, for example, Bluetooth® or Wi-Fi™ connections.

According to some example embodiments, the communications interface 140 may be configured to interface with, for example, a patient support apparatus 141. The patient support apparatus 141 may be, for example, a bed that is controllable to cause a patient within the bed to move to prevent pressure ulcers. According to some example embodiments, via the communications interface 140, the processing circuitry 110 may be configured to control movement of the patient support apparatus 141 by, for example, transmitting instructions to move the patient support apparatus 141 to cause the patient to move and prevent pressure ulcers. The patient support apparatus 141 may be movable by causing an air mattress device of the patient support apparatus 141 to adjust air chamber pressures to locally relieve pressure on the patient at select locations, such as those locations where an ischemia event is detected as further described below.

The user interface 150 may be controlled by the processing circuitry 110 to interact with a user. In this regard, via the user interface 150, the processing circuitry 110 may be configured to output information to a user via an output device such as, for example, driving a display 151 or an audio device 152 (e.g., to sound an alert) and receive information input from a user via an input device such as, for example, a keyboard, mouse, touch screen, or the like.

The EMG sensor 160 may be comprised of two or more electrodes between which the EMG sensor may be configured to measure a voltage or potential difference. According to some example embodiments, the EMG sensor 160 may be operatively coupled to amplifiers (e.g., with a gain of 5000 and possibly adjusted to avoid clipping) to generate an output signal that can be analyzed. According to some example embodiments, a complex array of electrodes may be used. The electrodes of the EMG sensor may be affixed to the surface of the skin of a patient to detect electrical activity in muscle tissue of interest. According to some example embodiments, the electrodes may penetrate the skin to be placed in direct contact with internal muscle tissue such as muscle. Via the electrodes, the EMG sensor 160 may be configured to assess muscle tissue function (e.g., muscle function) by detecting voluntary and involuntary muscle activity. In this regard, the EMG sensor 160 may be configured to monitor involuntary muscle activity that occurs regularly, even when the muscle is at rest, where such involuntary muscle activity is also referred to as muscle tone.

As indicated above, a raw EMG signal from the sensor may be measured in volts since a changing potential difference related to the movement of the muscle tissue can be captured. This potential difference or voltage may have components at a number of different frequencies. As such, as further described below, the EMG signal may be analyzed in the frequency domain where a power contribution at different frequencies can be determined and analyzed.

Figure 2:
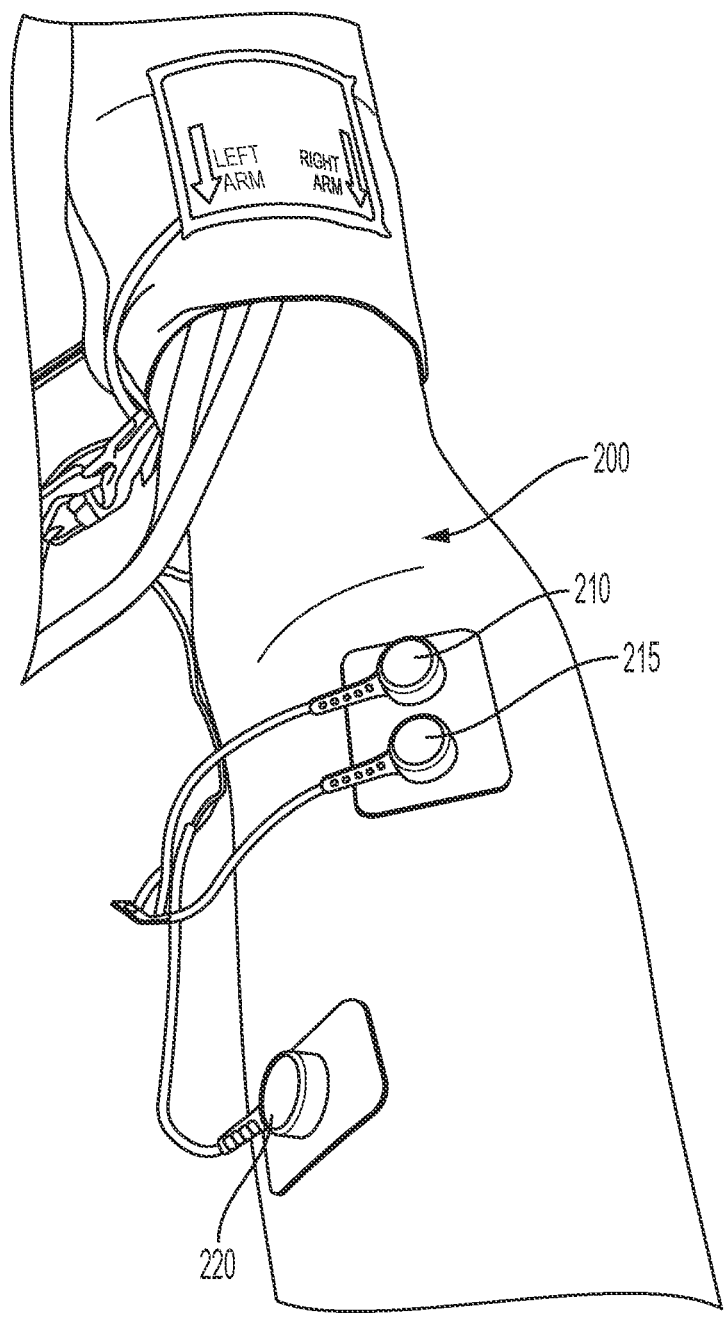
FIG. 2 is an image of an application of electrodes of an EMG sensor on the skin of a patient according to some example embodiments.

With reference to FIG. 2, an EMG sensor with three electrodes 210, 215, and 220 is shown applied to the lower arm in an example application to a patient. The electrodes 210, 215, and 220 may be, for example, silver-silver chloride EMG electrodes, and may be affixed to the surface of the patient's 200 skin. The electrodes 210, 215, and 220 may be positioned to detect electrical activity in muscle tissue of interest, in this case, a muscle in the arm of the patient 200 (i.e., the brachioradialis on the lower arm). EMG electrodes 210 and 215 may be placed approximately one inch apart over or immediately over the muscle of interest and a ground electrode 220 may be placed away from the muscle of interest, as shown in FIG. 2. The potential difference detected by the electrodes 210 and 215 may be determined relative to the ground electrode 220. The resultant signals from the electrodes 210, 215, and 220 may be provided to a processing circuitry, such as processing circuitry 110, as EMG sensor signals for analysis.

As mentioned above, the output signal of the EMG sensor can be analyzed to detect whether an ischemia event may be occurring via analysis of the EMG sensor signals by the processing circuitry 110. To describe the techniques and configuration of the ischemia detector 100, tests and the results of the tests are described herein. In this regard, tests were performed using a blood pressure cuff to control the flow of blood to an area, for example, the arm, to induce an ischemia event so that detection of the ischemia event may be performed. In this regard, the blood pressure cuff operates as a tourniquet to restrict blood flow in a controllable manner to facilitate performing the test and the creation of a controlled ischemia event.

The test is performed in three time phases over a duration of 300 seconds. In the baseline phase, from 0 to 60 seconds, no pressure is provided by the cuff and therefore a baseline signal is generated. During the ischemic phase, from 60 to 180 seconds, the blood pressure cuff is inflated to block blood circulation in the arm and thus an ischemia event is occurring. A pulse oximeter may also be applied to the finger of the test subject (due to blood flow to the finger also being affected by the inflated cuff) to confirm the absence of blood flow and thus the occurrence of an ischemia event. In the recovery phase, from 180 to 300 seconds, the blood pressure cuff is deflated thereby allowing blood flow back into the arm to cause a recovery to the affected muscles and other soft tissue.

Figure 3:
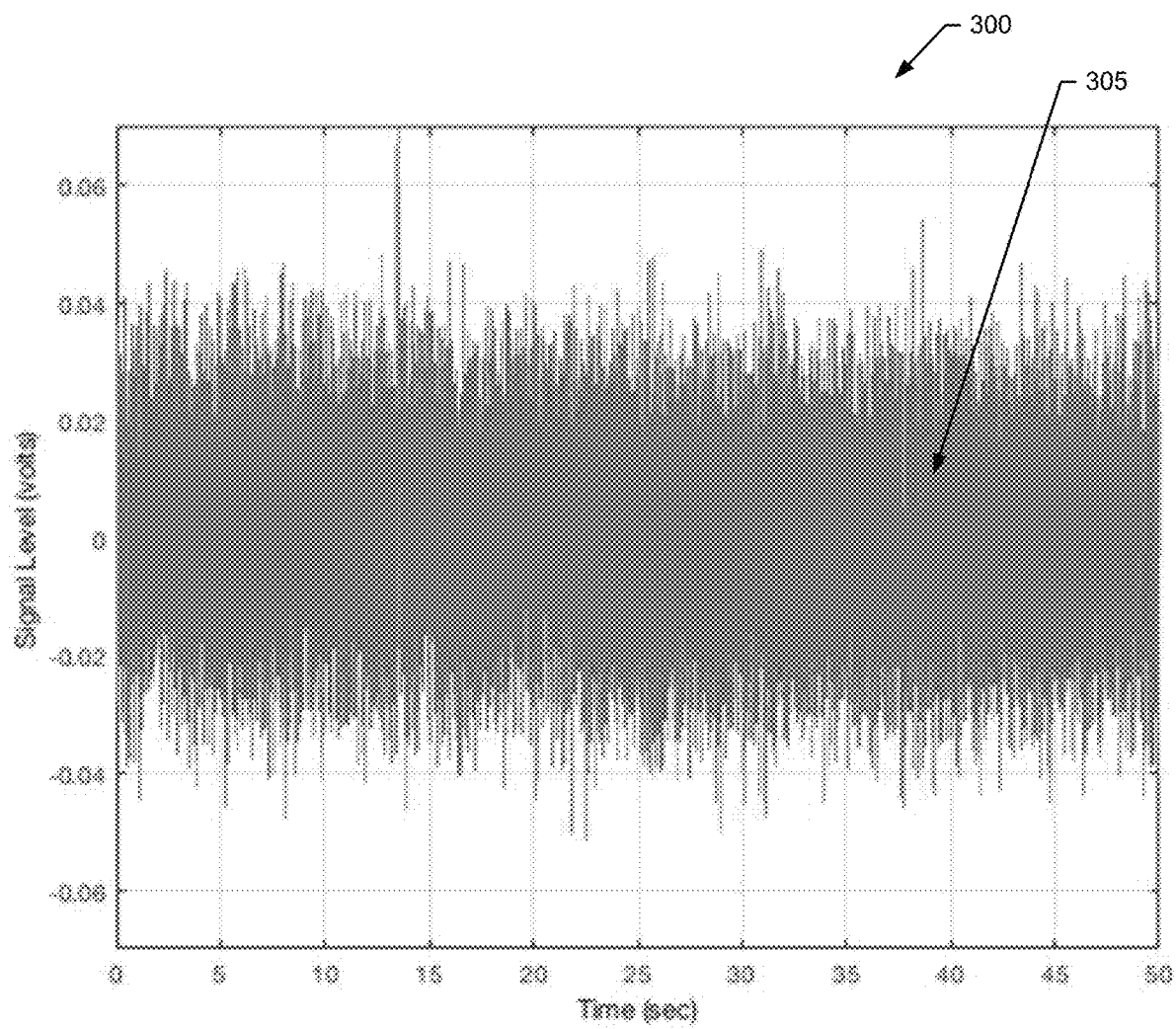
FIG. 3 is a chart of an voltage output signal of an EMG sensor over time according to various example embodiments.

Referring now to FIG. 3, a chart 300 is provided of the EMG signal 305 during the baseline phase of the test. The EMG signal 305, as a time series signal, is shown to fluctuate between about 0.04 volts to −0.04 volts over time. Although not shown, as the test moves into the ischemia phase observable differences in the EMG signal 305 in the time domain were not readily observable, but further analysis may be performed to reveal relationships between the signal power at various frequencies and in certain frequency bands.

When the EMG signal is transformed via, for example, a fast Fourier transform, into the frequency domain, a different analysis may be performed that more readily distinguishes the phases. In this regard, to transform the time series data of chart 300 into the frequency domain, a fast Fourier Transform may be performed on successive slices or chunks of the time series data. According to some example embodiments, a number of samples may be considered within each slice or chunk, such as, for example, 1024 samples. As a result of the data transformation, a difference in the EMG power level may be more readily identified at various frequencies between the baseline phase and the ischemic phase. Further, the EMG power level in the frequency domain can also be used to differentiate the recovery phase.

Figure 4:
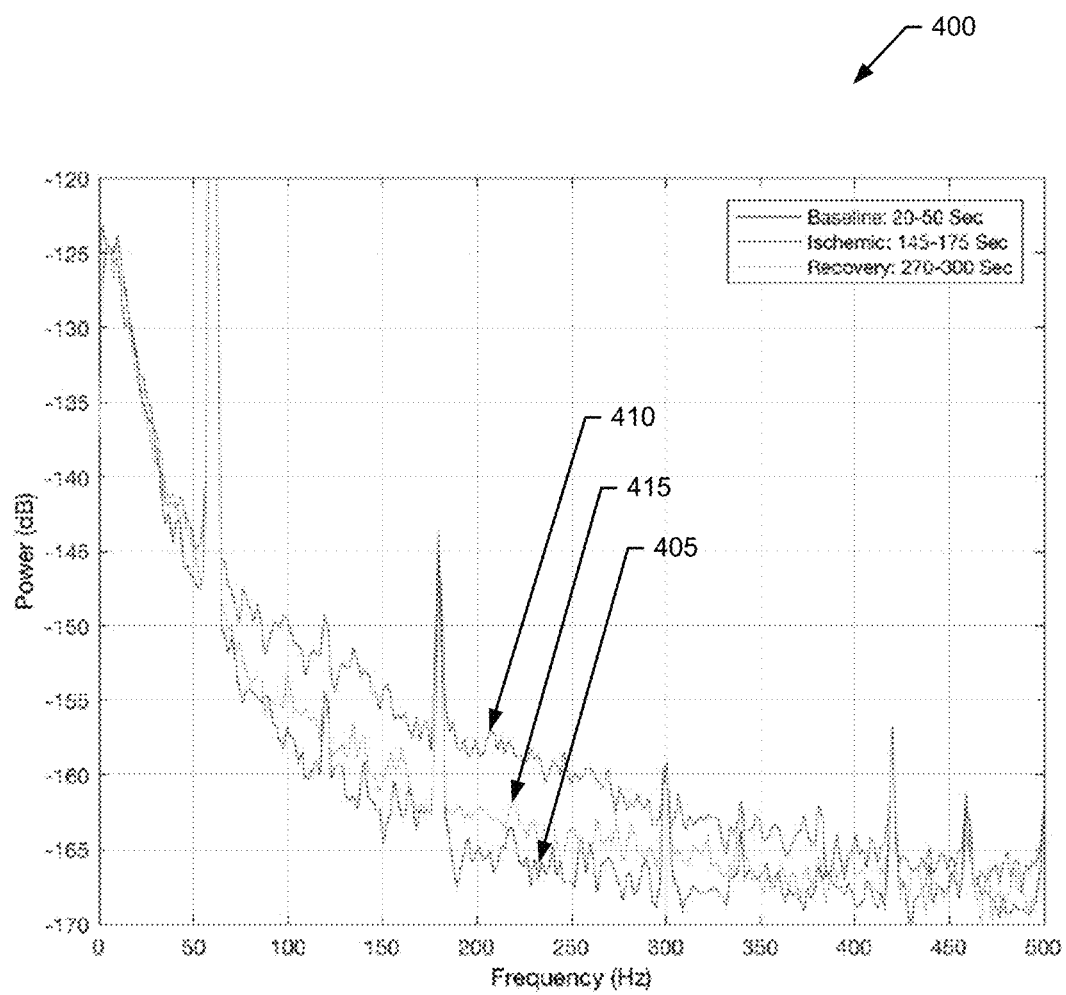
FIG. 4 is a chart of a signal power levels from an EMG sensor at various frequencies during different test phases according to various example embodiments.

With reference to FIG. 4, the EMG power level is shown in the chart 400 in each of the test phases. The power level is plotted as a function of frequency for the three phases or time periods. In this regard, the EMG power level during the baseline phase is shown at 405. Further, the EMG power level during the ischemic phase is shown at 410. Finally, the EMG power level during recovery is shown at 415. It can be seen from the chart 400 that the EMG power level during the ischemia phase is higher than the EMG power level during the baseline phase (e.g., by about 7 to 8 dB at about 200 Hz). Further, the EMG power level in the recovery phase is also higher than the EMG power level during the baseline phase (e.g., by about 2 to 3 dB at about 200 Hz), but also lower than the EMG power level during the ischemic phase (e.g., by about 4 or 5 dB at about 200 Hz). The EMG power levels for each phase tend to converge above 400 Hz and below 60 Hz, thereby offering little in the way of usable differentiation at these frequencies. However, it can be seen that the EMG power level 75 to 275 Hz shows useful differentiation with rather clear distinctions being observable over the 200 to 250 Hz band, which has been shown to be repeatable within these frequencies. As such, the differences in the EMG power level in the frequency domain can therefore be leveraged to distinguish between the phases of the test and can thus be used to detect an ischemia event in actual practice.

Figure 5A:
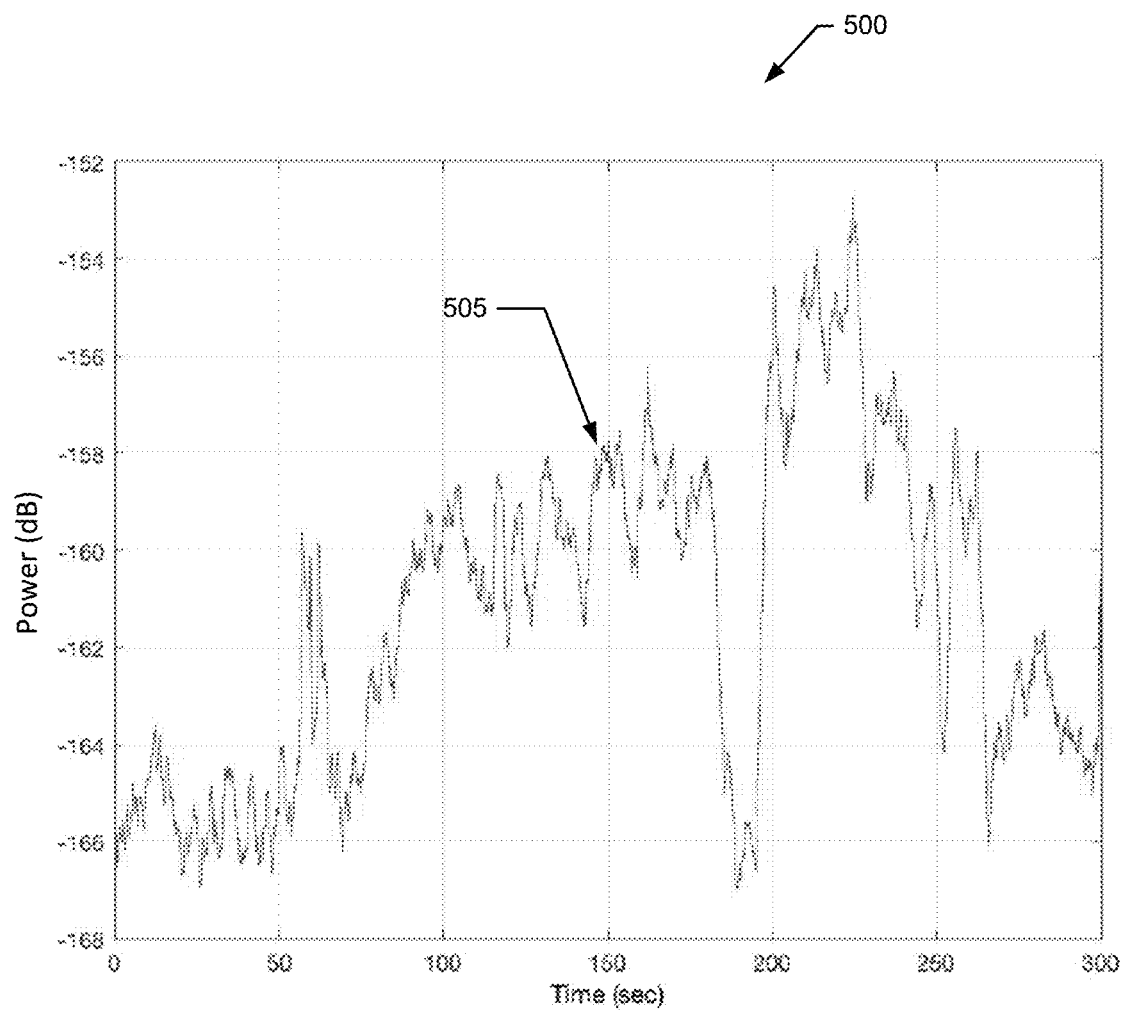
FIG. 5A is a chart of a single power output from an EMG sensor over time according to various example embodiments.
Figure 5B:
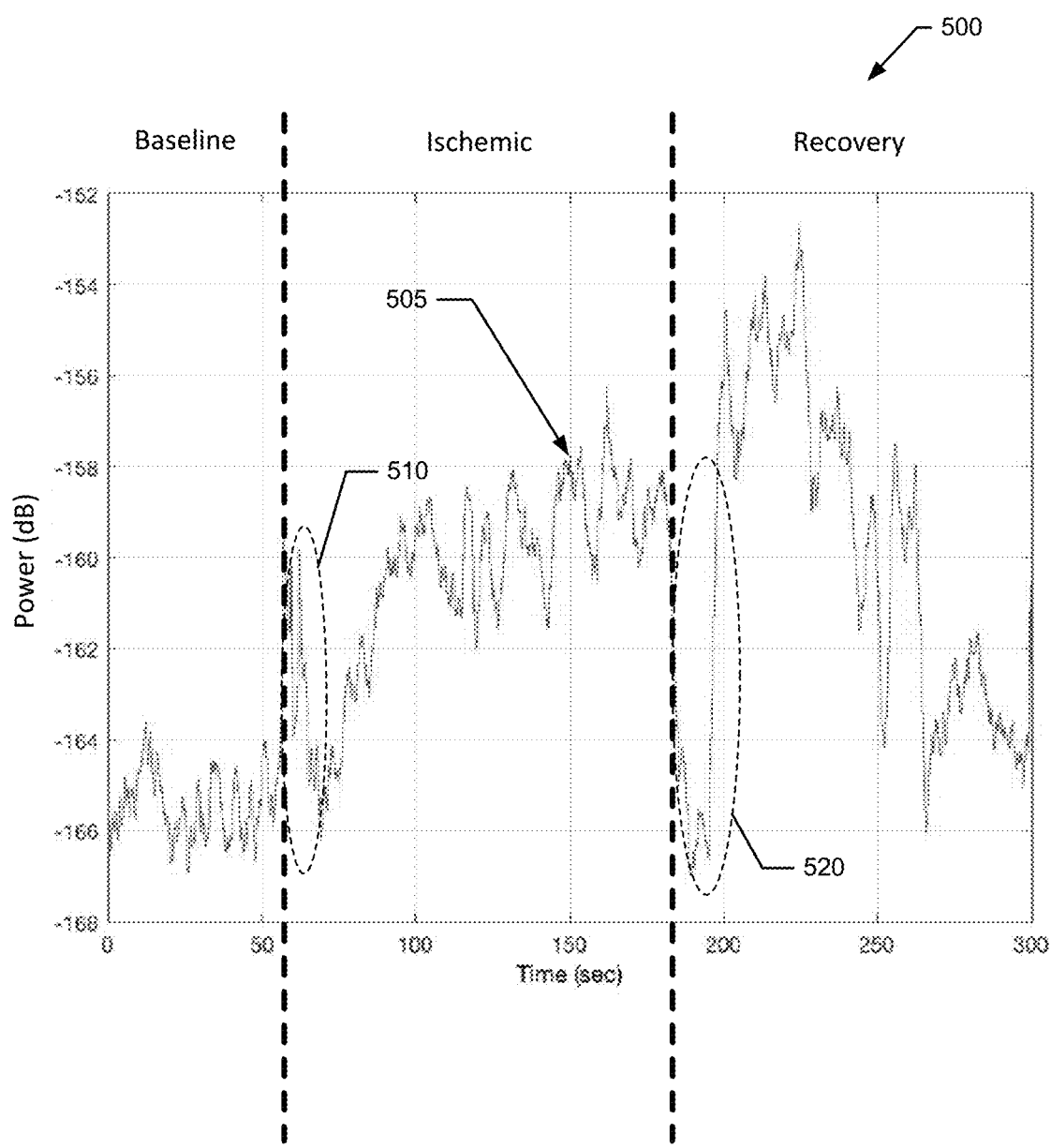
FIG. 5B is the chart of 5A with explanatory markups according to various example embodiments.

FIGS. 5A and 5B also show yet another variation of the transformed data plotted as the EMG power level, with respect to time for the band of frequencies between 200 and 250 Hz. The data of plot 505 may be generated by computing the average signal power level for the 200 to 250 Hz range for each time-to-frequency transformation. The chart 500 as shown in FIG. 5A is shown with no markings to provide a clear view of the plot 505, while the same chart 500 shown in FIG. 5B is shown with markings to facilitate discussion of the plot 505. In this regard, with reference to FIG. 5B, the vertical dotted lines indicate the transition time between the phases of the test.

During the baseline portion of the plot 505, the power level is fairly stable until the transition at 60 seconds, when the blood pressure cuff is inflated. At 60 seconds, in the region 510, the spike in the power level is attributable to the movement associated with inflation of the cuff, and is therefore not relevant to the processing in an actual implementation. From about 70 to 100 seconds, the power level gradually increases by about 5 dB due to oxygen depletion and the onset of the ischemia. Between 100 to 180 seconds, the power level increases with a smaller slope and includes an increase in variability. The test subject indicated a feeling of numbness at about 120 seconds, which may have caused some volatility due to associated involuntary muscle movement. At 180 seconds, the cuff is deflated causing the downward spike at region 520, which again is not relevant to the analysis. After the spike in region 520, recovery occurs and the power level continues to increase. This continued increase may be a residual continuation of the ischemic effect as reperfusion occurs. At about 225, a sudden drop in the power level occurs from about −153 dB to −159 dB, which is likely the effect of deoxygenated blood being fully exchanged with oxygenated blood in the muscle tissue. At about 275 seconds, reperfusion during recovery may be complete and the power level returns to baseline levels.

Leveraging the relationship between the EMG signal power level at certain frequencies and in certain frequency bands and the oxygen depletion in a muscle tissue of interest, the processing circuitry 110 may be configured to detect ischemia events via the EMG sensor 160. Accordingly, the processing circuitry 110 may be configured to perform various functionalities to achieve the technical result of detecting an ischemia event. In an example embodiment, the processing circuitry 110 may be embodied as, include or otherwise control, the ischemia detector 100 to perform various functionalities as described herein. As such, in some embodiments, the processing circuitry 110 may be said to cause each of the operations described in connection with, for example, method described by the flowchart of FIG. 6 and the associated example method. The processing circuitry 110 may therefore undertake the corresponding functionalities responsive to execution of instructions or algorithms configuring the processing circuitry 110 accordingly. The processing circuitry 110 may provide programmable control signals, selections, and the like to control the operation of the ischemia detector 100 responsive to execution of instructions stored in the memory.

Figure 6:
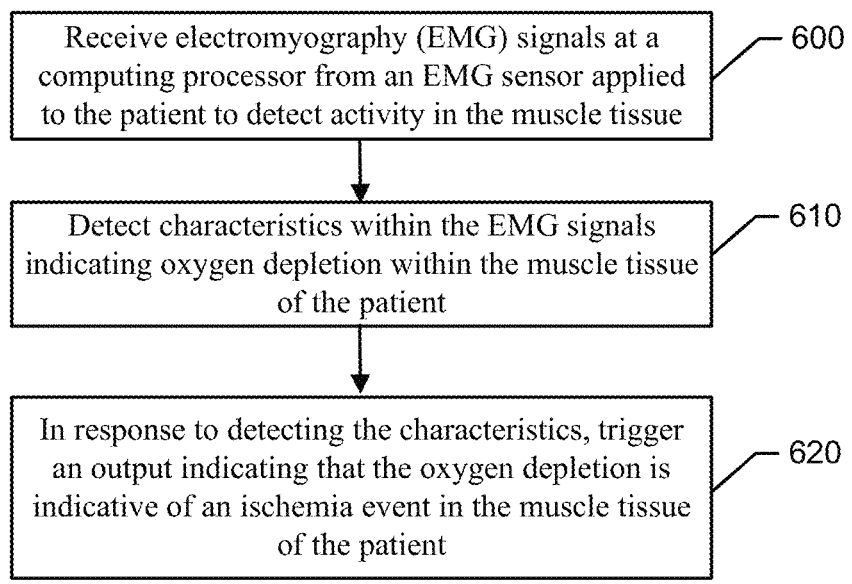
FIG. 6 shows an exemplary block diagram of a method for detecting an ischemia event in muscle tissue of a patient according to various example embodiments.

In this regard, the processing circuitry 110 may be configured to perform the operations of the example method described with respect to FIG. 6 to detect an ischemia event in the muscle tissue (e.g., muscle) of the patient. At 600, the processing circuitry 110 may be configured to receive electromyography (EMG) signals at the processing circuitry 110 from an EMG sensor applied to the patient to detect electrical activity in the muscle tissue. The electrical activity may be detected as electrical signals in the muscle tissue that are indicative of muscle status or activity. The processing circuitry 110 may also be configured to, at 610, detect characteristics within the EMG signals indicating oxygen depletion within the muscle tissue of the patient. The EMG signals may be received at the processing circuitry 110 directly or indirectly. Further, the detection of characteristics may be performed on the EMG signals as provided by the EMG sensor or in a processed form (e.g., transformed into the frequency domain). In this regard, the characteristics may include the signal power level of the EMG signals increasing by at least a threshold value at a select frequency or with respect to a select band of frequencies. In this regard, the characteristics may include the signal power level of the EMG signals increasing by at least a threshold value at a selected frequency (e.g., 200 Hz or about 200 Hz) or frequency band (e.g., 200 Hz to 250 Hz or about 200 Hz to 250 Hz). According to some example embodiments, the processing circuitry 110 may also be configured to, at 620, trigger an output indicating that the oxygen depletion is indicative of an ischemia event in the muscle tissue of the patient in response to detecting the characteristics.

According to some example embodiments, triggering the output may include initiating an alert to health care personnel to physically reposition the patient by rendering an alert on a display (e.g., display 151) or sounding an alert on an audio device (e.g., audio device 152). According to some example embodiments, triggering the output may additionally or alternatively involve controlling movement of a patient support apparatus (e.g., patient support apparatus 141) to move the patient into a different physical position. In this regard, according to some example embodiments, controlling movement may include transmitting instructions to an air mattress device of the patient support apparatus 141 to adjust in air chamber pressures and locally relieve pressure on the patient at select locations. Further, according to some example embodiments, the processing circuitry may be further configured to continue to analyze subsequent EMG signals from the EMG sensor to determine whether the physical repositioning of the patient caused the muscle tissue to recover from the ischemia event.

According to some example embodiments, the detected characteristics of the EMG power level signal for triggering the output may further include the signal power level increasing by the threshold value and exceeding the threshold value for a selected duration of time, possibly at a selected frequency or frequency band. According to some example embodiments, the threshold value may be defined as a change from a baseline power level to an ischemic power level, which may be set as a threshold value of, for example, 5 dB or about 5 to 10 dB. Further, the selected duration of time for exceeding the threshold increase may be set to, for example, a value between 25 to 50 seconds. In this regard, according to some example embodiments, the processing circuitry 110 may be configured to implement a timer to determine whether the selected duration of time has elapsed, and reset the timer in an instance in which the signal power level does not remain above the threshold value for the selected duration of time. In this regard, once the signal power level exceeds the threshold value increase, the signal power may be required to remain above the threshold value increase for the selected duration of time before an output may be triggered indicating that an ischemia event is occurring. According to some example embodiments, the signal power level may be generated as an average signal power determined, for example, via ensemble averaging, over a frequency range. Further, other noise reducing and filtering techniques may be employed to remove irrelevant anomalies from the power level signal.

Additionally, the processing circuitry 110 may be configured to continue to monitor the EMG signal after repositioning has occurred to determine whether the repositioning was successful in alleviating the ischemia event and causing the muscle tissue to recover. In this regard, either via detection by the EMG sensor 160 (or another sensor) or by receiving and indication from, for example, a user via the user interface 150, the processing circuitry 110 may be configured to determine that a repositioning effort is complete. Subsequently, the processing circuitry 110 may be configured to continue to analyze the power level of the EMG signal to determine that the ischemia event has ended and a recovery of the muscle tissue is occurring. In this regard, the processing circuitry 110 may be configured to determine, after having determined that an ischemia event has occurred, if the power level has decreased by a threshold value (e.g., 5 to 10 dB), for example, from a peak at a selected frequency or frequency band and/or a return to the pre-ischemia event baseline. Such a drop in the power level may be indicative of an end of the ischemia event, the recovery of the muscle tissue, and thus the success of the repositioning.

Figure 7:
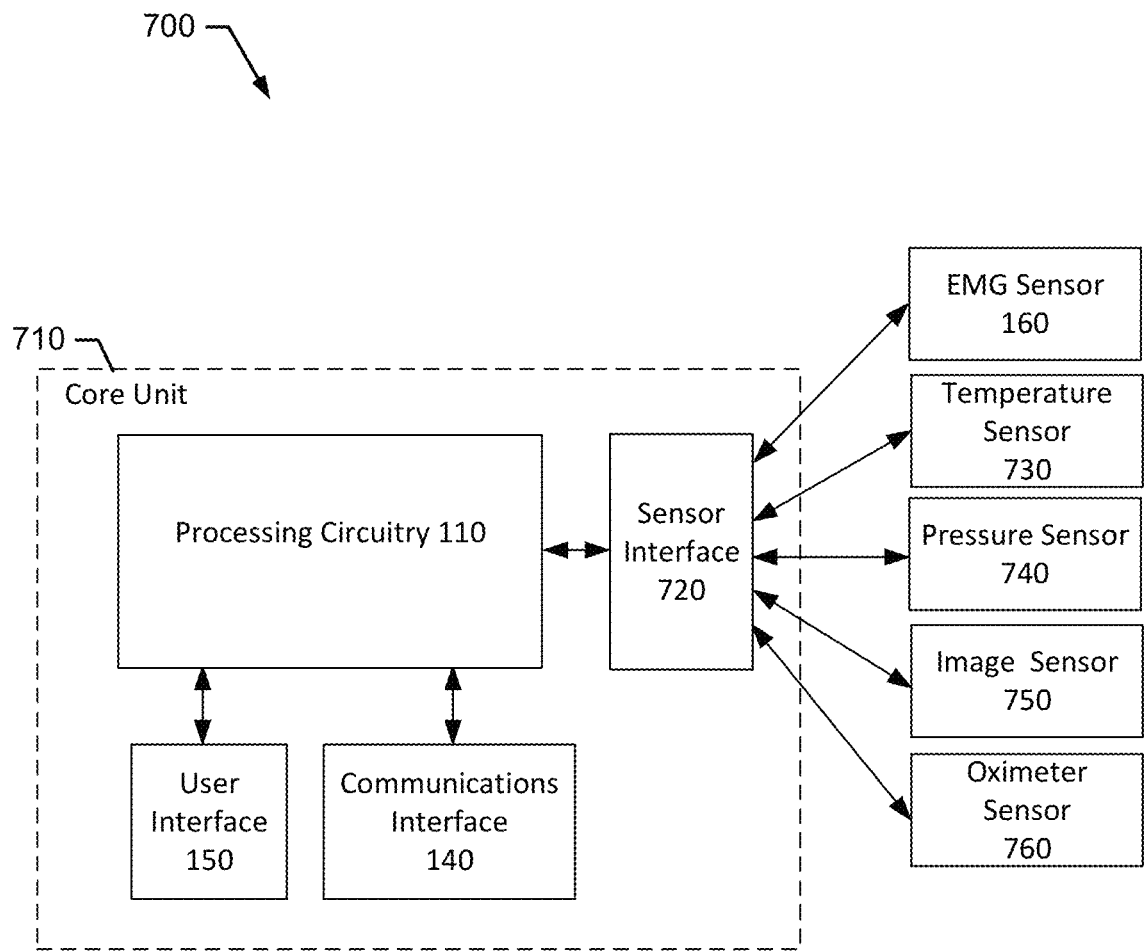
FIG. 7 illustrates a block diagram of an example system including a plurality of sensors according to some example embodiments.

Now referring to FIG. 7, an example system 700 for detecting an ischemia event in muscle tissue of a patient is provided. The example system may include a core unit 710 that may be operably coupled to a plurality of sensors. The core unit 710 may be configured to operate in the same or similar manner as the ischemia detector 100, although with the EMG sensor 160 operating as a peripheral device via a sensor interface 720. In this regard, the core unit 710 may include the processing circuitry 110, which may include a memory and a processor as described above. Also, the core unit 710 may include the user interface 150 and the communications interface 140, both of which may be configured to be operated as described above. However, the sensor interface 720 may be circuitry that may be external to or embodied by processing circuitry 110. The sensor interface 720 may, for example, be a multiplexing-type device that permits any number of sensors to interact with the processing circuitry 110, including EMG sensor 160 as described above. As such, the example system 700 may include a plurality of sensors outputting a plurality of respective signals to the sensor interface 720 and ultimately to the processing circuitry 110 for analysis to determine if an ischemia event is occurring on the muscle tissue of a patient. According to some example embodiments, the plurality of sensors may include a temperature sensor 730, a pressure sensor 740, an image sensor 750, or an oximeter sensor 760.

As such, the processing circuitry 110 may be configured to control and receive feedback from a variety of sensors to determine whether an ischemia event is occurring. In this regard, the processing circuitry 110 may be configured to receive respective signals from the plurality of sensors. According to some example embodiments, the respective signals may include EMG signals from the EMG sensor 160. The EMG sensor 160 may be configured to detect electrical signals in the muscle tissue that are indicative of muscle status or activity. The EMG signals may be received at the processing circuitry 110 directly or indirectly. The processing circuitry 110 may also be configured determine an EMG factor by detecting characteristics within the EMG signals indicating oxygen depletion within the muscle tissue of the patient. The detection of characteristics may be performed on the EMG signals as provided by the EMG sensor 160 or in a processed form (e.g., transformed into the frequency domain). The characteristics (as described above) may include the signal power level of the EMG signals in the frequency domain increasing by at least a threshold value. The processing circuitry 110 may also be configured to integrate the EMG factor with other factors to determine whether an ischemia event is occurring in the muscle tissue of the patient. In this regard, the other factors may be based on the respective signals from the other sensors within the plurality of sensors. For example, if a majority of the factors including the EMG factor are true (i.e., supporting the finding of an ischemia event), then an ischemia event may be determined. If, however, the EMG factor or a majority of factors are false (i.e., not supporting the finding of an ischemia event), then no ischemia event may be determined. Again, the processing circuitry 110 may also be configured to trigger an output indicating that the ischemia event is occurring in the muscle tissue of the patient based on the integration of the EMG factor with the other factors.

According to some example embodiments, a plurality of EMG sensors may be employed and operably coupled to the processing circuitry 110. In this regard, respective EMG sensors may be placed to monitor different muscles, for example, in a general area of a body. In situations where an ischemia event may be detectable in multiple muscles, the plurality of EMG sensors may be employed to both detect and confirm the detection of the ischemia event by integrating the EMG factors for each of the EMG sensors.

With respect to considering the outputs of other sensors, according to some example embodiments, the pressure sensor 740 may be operably coupled to the patient and configured to output pressure sensor signals indicative of a pressure measurement between the patient and a surface. With the inclusion of the pressure sensor, the processing circuitry 110 may be further configured to receive the pressure sensor signals from the pressure sensor 740 as one of the respective signals, and generate a pressure sensor factor based on the pressure sensor signals. In this regard, the pressure sensor factor may be related to detection of the ischemia event, and the pressure sensor factor may be one of the other factors integrated with the EMG factor. According to some example embodiments, the pressure sensor factor may be a binary determination that indicates that a pressure event that may be indicative of an ischemia event is occurring or not. To detect a pressure event, the pressure sensor signals may be analyzed to determine if a pressure point or area on the patient's body has exceeded a pressure threshold value, possibly for a selected duration of time. If the pressure point or area on the patient's body has exceeded a pressure threshold value, possibly for a selected duration of time, the pressure factor may be true thereby increasingly the likelihood of determining that an ischemia event has occurred as a result of the factor integration. However, if a pressure point or area on the patient's body has not exceeded a pressure threshold value, possibly for a selected duration of time, the pressure factor may be false thereby decreasing the likelihood of determining that an ischemia event has occurred as a result of the factor integration.

According to some example embodiments, the temperature sensor 730 may be operably coupled to the patient and configured to output temperature sensor signals indicative of a temperature measurement near or immediately above the muscle tissue of interest. With the inclusion of the temperature sensor, the processing circuitry 110 may be further configured to receive the temperature sensor signals from the temperature sensor 730 as one of the respective signals, and generate a temperature sensor factor based on the temperature sensor signals. In this regard, the temperature sensor factor may be related to detection of the ischemia event, and the temperature sensor factor may be one of the other factors integrated with the EMG factor. According to some example embodiments, the temperature sensor factor may be a binary determination that indicates that a temperature event that may be indicative of an ischemia event is occurring or not. To detect a temperature event, the temperature sensor signals may be analyzed to determine if a temperature on the skin of the patient near or immediately over the muscle tissue of interest has decreased below a threshold value, possibly for a selected duration of time, which may be indicative of a lack of blood flow to the area. If the temperature on the skin near or immediately over the muscle tissue of interest has dropped below threshold value, possibly for a selected duration of time, the temperature factor may be true thereby increasing the likelihood of determining that an ischemia event has occurred as a result of the factor integration. If the temperature on the skin near or immediately over the muscle tissue of interest has not dropped below a threshold value, possibly for a selected duration of time, the temperature factor may be false thereby decreasing the likelihood of determining that an ischemia event has occurred as a result of the factor integration.

According to some example embodiments, the image sensor 750 may be operably coupled to the patient and configured to output image sensor signals indicative of a repeated image capture near or immediately over the muscle tissue of interest. With the inclusion of the image sensor 750, the processing circuitry 110 may be further configured to receive the image sensor signals from the image sensor 750 as one of the respective signals, and generate an image sensor factor based on the image sensor signals. In this regard, the image sensor factor may be related to detection of the ischemia event, and the image sensor factor may be one of the other factors integrated with the EMG factor. According to some example embodiments, the image sensor factor may be a binary determination that indicates that a skin discoloration event based on spectral characteristics of the captured images that may be indicative of an ischemia event is occurring or not. To detect a skin discoloration event, the image sensor signals may be analyzed to determine if skin coloration has changed such that the skin coloration is reduced near or immediately over the muscle tissue of interest below a threshold value, possibly for a selected duration of time, which may be indicative of a lack of blood flow to the area. If the skin coloration near or immediately over the muscle tissue of interest has dropped below threshold value, possibly for a selected duration of time, the image sensor factor may be true thereby increasingly the likelihood of determining that an ischemia event has occurred as a result of the factor integration. If the skin coloration near or immediately over the muscle tissue of interest has not reduced below a threshold value, possibly for a selected duration of time, the image sensor factor may be false thereby decreasing the likelihood of determining that an ischemia event has occurred as a result of the factor integration.

According to some example embodiments, the oximeter sensor 760 may be operably coupled to the patient and configured to output oximeter sensor signals indicative of an oxygen content in the blood near or immediately over the muscle tissue of interest. According to some example embodiments, the oximeter sensor 760 may be, for example, a pulse oximeter. With the inclusion of the oximeter sensor 760, the processing circuitry 110 may be further configured to receive the oximeter sensor signals from the oximeter sensor 760 as one of the respective signals, and generate an oximeter sensor factor based on the oximeter sensor signals. In this regard, the oximeter sensor factor may be related to detection of the ischemia event, and the oximeter sensor factor may be one of the other factors integrated with the EMG factor. According to some example embodiments, the oximeter sensor factor may be a binary determination that indicates whether a low blood oxygen event that may be indicative of an ischemia event is occurring or not. To detect a low blood oxygen event, the oximeter sensor signals may be analyzed to determine if a blood oxygen level is below a threshold value, possibly for a selected duration of time, which may be indicative of a lack of blood flow to the area. If the blood oxygen level near or immediately over the muscle tissue of interest has dropped below threshold value, possibly for a selected duration of time, the oximeter sensor factor may be true thereby increasingly the likelihood of determining that an ischemia event has occurred as a result of the factor integration. If the blood oxygen level near or immediately over the muscle tissue of interest has not reduced below a threshold value, possibly for a selected duration of time, the oximeter sensor factor may be false thereby decreasing the likelihood of determining that an ischemia event has occurred as a result of the factor integration.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. In cases where advantages, benefits or solutions to problems are described herein, it should be appreciated that such advantages, benefits and/or solutions may be applicable to some example embodiments, but not necessarily all example embodiments. Thus, any advantages, benefits or solutions described herein should not be thought of as being critical, required or essential to all embodiments or to that which is claimed herein. Although specific terms are employed herein, they are used in a generic and descriptive sense only and not for purposes of limitation.

That which is claimed:

1. An apparatus for detecting an ischemia event, in muscle tissue of a patient, that is not externally visible to an unaided human eye, the apparatus comprising:
    an electromyography (EMG) sensor configured to be applied to skin of the patient at a position over the muscle tissue to detect electrical activity in the muscle tissue and generate EMG signals corresponding to the electrical activity detected in the muscle tissue;
    a processing circuitry in communication with the EMG sensor, the processing circuitry configured to:
        receive the EMG signals from the EMG sensor;
        detect an ischemia event in the muscle tissue of the patient by detecting characteristics within the EMG signals that indicate oxygen depletion within the muscle tissue of the patient, wherein the characteristics comprise a signal power level of the EMG signals, wherein, to detect the characteristics that indicate oxygen depletion within the muscle tissue of the patient, the processing circuitry is further configured to:
            transform the EMG signals into a frequency domain; and
            determine whether the signal power level of the transformed EMG signals at a select frequency increases by more than a first threshold value from a baseline signal power indicating the ischemia event;
        trigger an output in response to detecting the characteristics indicating the ischemia event in the muscle tissue of the patient; and
        continue to analyze subsequent EMG signals from the EMG sensor to determine whether the muscle tissue is in recovery from the ischemia event by detecting characteristics of the subsequent EMG signals including a signal power level of the subsequent EMG signals decreasing from above the first threshold value by at least a second threshold value at the select frequency and remaining above the baseline signal power, the second threshold value being less than the first threshold value; and an output device in communication with the processing circuitry, the output device configured to:
receive an output from the processing circuitry in response to the processing circuitry detecting the ischemia event; and
display or sound an alert indicating the ischemia event.

2. The apparatus of claim 1, wherein the output device is a display or an audio device and the alert instructs health care personnel to physically reposition the patient.

3. The apparatus of claim 1, further comprising:
a patient support apparatus in communication with the processing circuitry, wherein triggering the output includes the processing circuitry transmitting instructions to the patient support apparatus to control movement of the patient support apparatus to move the patient into a different physical position.

4. The apparatus of claim 3, wherein the patient support apparatus comprises an air mattress device that receives instructions from the processing circuitry to adjust air chamber pressures of the mattress to locally relieve pressure on the patient at a location where the ischemia event was detected.

5. The apparatus of claim 1, wherein the detected characteristics further include the signal power level increasing by the first threshold value-for a selected duration of time.

6. The apparatus of claim 5, wherein processing circuitry is further configured to implement a timer to determine whether the selected duration of time has elapsed, wherein the processing circuitry is further configured to reset the timer in an instance in which the signal power level does not remain above the first threshold value for the selected duration of time.

7. The apparatus of claim 1, wherein the detected characteristics include the signal power level at the select frequency being an average signal power level.

8. The apparatus of claim 1, wherein the processing circuitry is configured to determine the baseline signal power over a baseline duration of time.

9. The apparatus of claim 1, wherein the first threshold value is 5 dB to 10 dB and the select frequency is between 200 Hz to 250 Hz.

10. A method for detecting an ischemia event, in muscle tissue of a patient, that is not externally visible to an unaided human eye, the method comprising:
detecting, by an electromyography (EMG) sensor applied to skin of the patient at a position over the muscle tissue, electrical activity in the muscle tissue of the patient;
generating EMG signals, by the EMG sensor, corresponding to the electrical activity detected in the muscle tissue;
receiving the EMG signals at processing circuitry from an EMG sensor;
detecting, by the processing circuitry, an ischemia event in the muscle tissue of the patient by detecting characteristics within the EMG signals that indicate oxygen depletion within the muscle tissue of the patient, wherein the characteristics comprise signal power level of the EMG signals wherein detecting the characteristics that indicate oxygen depletion within the muscle tissue of the patient further comprises;
transforming the EMG signals into a frequency domain; and
determining whether the signal power level of the transformed EMG signals at a select frequency increases by more than a first threshold value from a baseline signal power indicating the ischemia event;
triggering an output in response to detecting the characteristics indicating the ischemia event in the muscle tissue of the patient; and
continuing to analyze, by the processing circuitry, subsequent EMG signals from the EMG sensor to determine whether the muscle tissue is in recovery from the ischemia event by detecting characteristics of the subsequent EMG signals including a signal power level of the subsequent EMG signals decreasing from above the first threshold value by at least a second threshold value at the select frequency and remaining above the baseline signal power, the second threshold value being less than the first threshold value.

11. The method of claim 10, wherein the detected characteristics further include the signal power level increasing by the first threshold value-for a selected duration of time.

12. The method of claim 11, further comprising:
implementing a timer to determine whether the selected duration of time has elapsed; and
resetting the timer in an instance in which the signal power level does not remain to be above the first threshold value for the selected duration of time.

13. The method of claim 10, wherein the detected characteristics include the signal power level at the select frequency being an average signal power level.

14. The method of claim 10, wherein the detected characteristics include the signal power level at the select frequency being an ensemble average signal power level over a select frequency range that includes the select frequency.

15. The method of claim 10, wherein triggering the output includes triggering the output to initiate an alert to health care personnel to physically reposition the patient.

16. The method of claim 10, wherein triggering the output includes triggering the output to control movement of a patient support apparatus to move the patient into a different physical position.

17. A system for detecting an ischemia event, in muscle tissue of a patient, that is not externally visible to an unaided human eye, the system comprising:
a plurality of sensors outputting a plurality of respective signals, the plurality of sensors including an electromyography (EMG) sensor configured to be applied to skin of the patient at a position over the muscle tissue to detect electrical activity in the muscle tissue and generate EMG signals corresponding to the electrical activity detected in the muscle tissue; and
a processing circuitry in communication with the plurality of sensors, the processing circuitry configured to:
receive the respective signals from the plurality of sensors, the respective signals comprising the EMG signals from the EMG sensor;
determine an EMG factor by detecting an ischemia event in the muscle tissue of the patient by detecting characteristics within the EMG signals that indicate oxygen depletion within the muscle tissue of the patient, wherein the characteristics comprise a signal power level of the EMG signals wherein, to detect the characteristics that indicate oxygen depletion within the muscle tissue of the patient, the processing circuitry is further configured to:
transform the EMG signals into a frequency domain; and
determine whether the signal power level of the transformed EMG signals at a select frequency increases by more than a first threshold value from a baseline signal power indicating the ischemia event;

integrate the EMG factor with other factors to determine whether the ischemia event is occurring in the muscle tissue of the patient, the other factors being based on the respective signals from other sensors within the plurality of sensors;

trigger an output indicating that the ischemia event is occurring in the muscle tissue of the patient based on an integration of the EMG factor with the other factors; and continue to analyze subsequent EMG signals from the EMG sensor to determine whether the muscle tissue is in recovery from the ischemia event by detecting characteristics of the subsequent EMG signals including a signal power level of the subsequent EMG signals decreasing from above the first threshold value by at least a second threshold value at the select frequency and remaining above the baseline signal power, the second threshold value being less than the first threshold value.

18. The system of claim 17, wherein the plurality of sensors includes an oximeter sensor operably coupled to the patient and configured to output oximeter sensor signals indicative of a blood oxygen level;

wherein the processing circuitry is further configured to:
receive the oximeter sensor signals from the oximeter sensor as one of the respective signals; and
generate a oximeter sensor factor based on the oximeter sensor signals, the oximeter sensor factor being related to detection of the ischemia event, and the oximeter sensor factor being one of the other factors integrated with the EMG factor.

19. The system of claim 17, wherein the plurality of sensors includes a temperature sensor operably coupled to the patient and configured to output temperature sensor signals indicative of a temperature measurement near the muscle tissue;

wherein the processing circuitry is further configured to:
receive the temperature sensor signals from the temperature sensor as one of the respective signals; and
generate a temperature sensor factor based on the temperature sensor signals, the temperature sensor factor being related to detection of the ischemia event, and the temperature sensor factor being one of the other factors integrated with the EMG factor.

20. The system of claim 17, wherein the plurality of sensors includes an image sensor operably coupled to the patient and configured to output image sensor signals indicative of an image capture near the muscle tissue;

wherein the processing circuitry is further configured to:
receive the image sensor signals from the image sensor as one of the respective signals; and
generate an image sensor factor based on the image sensor signals, the image sensor factor being related to detection of the ischemia event, and the image sensor factor being one of the other factors integrated with the EMG factor.

* * * * *